(12) United States Patent
Hansson et al.

(10) Patent No.: US 6,483,007 B1
(45) Date of Patent: *Nov. 19, 2002

(54) SANITARY NAPKIN AND A METHOD OF MANUFACTURING A SANITARY NAPKIN

(75) Inventors: Roy Hansson, Mölndal; Kerstin Johansson, Ulricehamn, both of (SE)

(73) Assignee: SCA Hygiene Products AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,634

(22) PCT Filed: Jun. 7, 1995

(86) PCT No.: PCT/SE95/00673

§ 371 (c)(1),
(2), (4) Date: Dec. 16, 1996

(87) PCT Pub. No.: WO96/01606

PCT Pub. Date: Jan. 25, 1996

(30) Foreign Application Priority Data

Jul. 11, 1994 (SE) ................................................ 9402448

(51) Int. Cl.[7] ................................................ A61F 13/15
(52) U.S. Cl. ........................ 604/369; 604/367; 604/378
(58) Field of Search ................................ 604/365–366, 604/369, 378–383, 385.1–387, 393–396; 156/164, 229

(56) References Cited

U.S. PATENT DOCUMENTS

| | | | | |
|---|---|---|---|---|
| 4,079,739 A | * | 3/1978 | Whitehead | 607/369 |
| 4,184,498 A | * | 1/1980 | France | 604/387 |
| 4,212,296 A | * | 7/1980 | Schaar | 602/59 |
| 4,534,354 A | * | 8/1985 | Bonner, Jr. et al. | 602/75 |
| 4,534,769 A | * | 8/1985 | De Jonckheere et al. | 604/369 |
| 4,752,349 A | * | 6/1988 | Gebel | 604/385.1 |
| 5,012,540 A | * | 5/1991 | Hockaday | 604/369 |
| 5,091,240 A | * | 2/1992 | Kajander et al. | 604/366 |
| 5,453,143 A | * | 9/1995 | Menard | 604/387 |
| 5,520,674 A | * | 5/1996 | Lavon et al. | 604/369 |
| 5,558,656 A | * | 9/1996 | Bergman | 604/378 |
| 5,591,148 A | * | 1/1997 | McFall et al. | 604/387 |
| 5,591,150 A | * | 1/1997 | Olsen et al. | 604/387 |
| 5,628,739 A | * | 5/1997 | Hsieh et al. | 604/387 |
| 5,690,610 A | * | 11/1997 | Ito et al. | 602/46 |

FOREIGN PATENT DOCUMENTS

| | | |
|---|---|---|
| DE | 0 085 729 | 8/1983 |
| EP | 0 335 253 | 10/1989 |
| EP | 0 572 033 | 12/1993 |
| SE | 9203445-3 | 12/1993 |
| WO | 94/10956 | 5/1994 |

* cited by examiner

Primary Examiner—John G. Weiss
Assistant Examiner—K. M. Reichle
(74) Attorney, Agent, or Firm—Burns, Doane, Swecker & Mathis, LLP

(57) ABSTRACT

A sanitary napkin having an absorbent body and a layer of compressible and resilient, essentially non-absorbent material located adjacent a surface of the absorbent body which lies distal to a body of a water in use. The layer of compressible and resilient material has a surface area extending entirely over the surface of the absorbent body. Further, the layer of compressible and resilient material is thicker in a longitudinal central region of the napkin than in remainder of the napkin and the layer of compressible and resilient material is resiliently compressible in a direction perpendicular to the surface of the absorbent body, so as to urge the sanitary napkin to fill out all available space between the sanitary napkin and the body of the wearer during use.

10 Claims, 2 Drawing Sheets

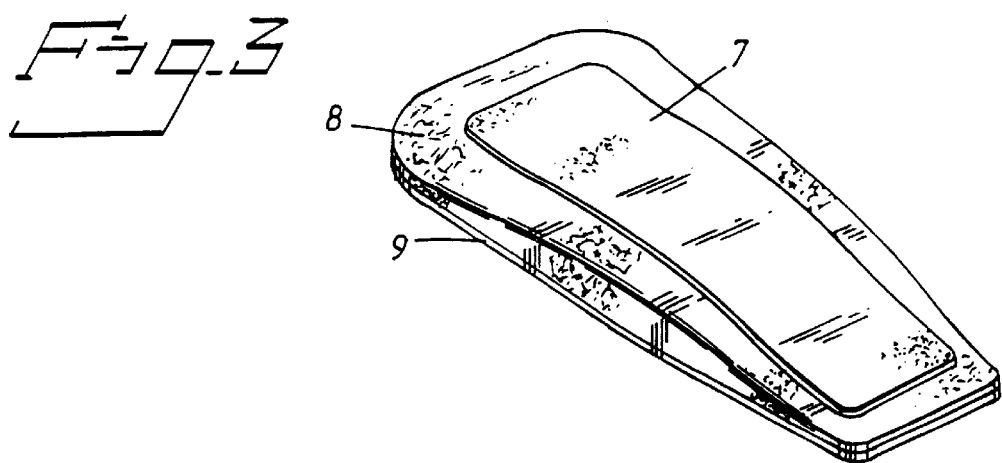
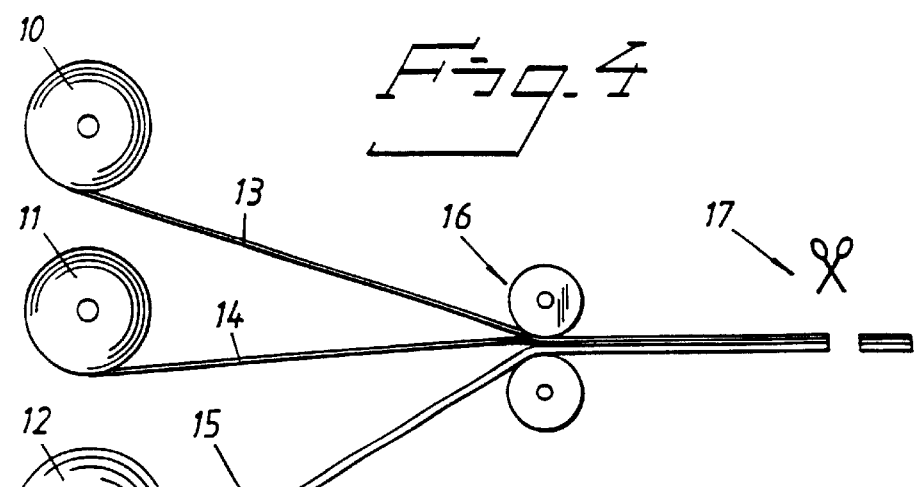
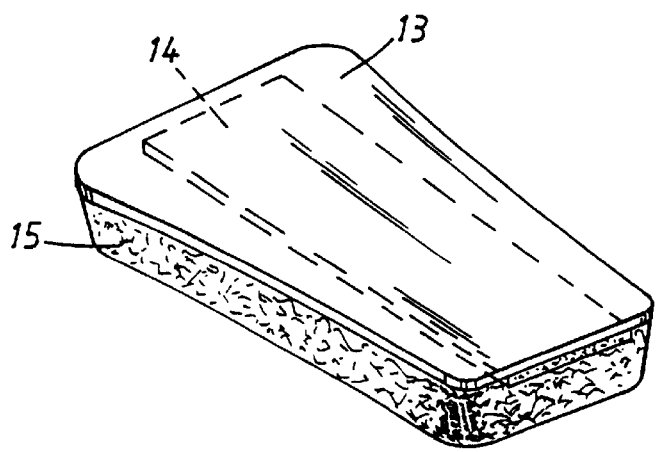

SANITARY NAPKIN AND A METHOD OF MANUFACTURING A SANITARY NAPKIN

TECHNICAL FIELD

The present invention relates to a sanitary napkin comprising an absorbent body, and also to a method for manufacturing such a sanitary napkin.

BACKGROUND OF THE INVENTION

The absorbent bodies included in present-day sanitary napkins normally have sufficient absorption capacity to take-up all menstrual fluid discharged by the wearer over the intended use time. Leakage of a sanitary napkin is usually due to factors other than the absorption capacity of the absorbent body. One such factor is the manner in which the napkin fits the wearer, since there is a serious risk of leakage should gaps or the like form between the wearer's body and the napkin after the napkin has been applied.

SUMMARY OF THE INVENTION

The primary object of the present invention is to reduce the risk of leakage caused by the formation of such gaps, while a secondary object is to reduce leakage caused by saturation of the absorbent body in local areas thereof.

These objects are achieved in accordance with the invention with a sanitary napkin which includes an absorbent body and which is characterized by a layer of compressible and resilient, essentially non-absorbent material placed adjacent that side of the absorbent body which lies distal to the wearer's body in use. When the sanitary napkin is worn, the layer of resilient material will urge the absorbent body against the wearer's body and therewith ensure that good body contact is obtained between napkin and user.

According to one preferred embodiment, the resilient layer also extends around the periphery of the absorbent body and is comprised of hydrophobic fibre wadding or porous foamed plastic. According to one variant, The layer of compressible and resilient material is thicker in a longitudinal central region of the napkin than in a remainder of the napkin. Thus, the resilient layer is thicker within the region of the wetting point than in other regions. The resilient layer is placed advantageously between the absorbent body and an outer casing sheet, which is preferably comprised of an air-permeable material. An inner casing sheet of liquid-permeable material is also placed adjacent that side of the absorbent body which lies distal to the resilient layer.

More particularly, the present invention relates to a sanitary napkin including an absorbent body, and a layer of compressible and resilient, essentially non-absorbent material located adjacent a surface of the absorbent body which lies distal to a body of a wearer in use, with the layer of compressible and resilient material having a surface area extending entirely over the surface of the absorbent body. The layer of compressible and resilient material is thicker in a longitudinal central region of the napkin than in a remainder of the napkin, and the layer of compressible and resilient material is resiliently compressible in a direction perpendicular to the surface of the absorbent body, so as to urge the sanitary napkin to fill out all available space between the sanitary napkin and the body of the wearer during use.

The invention also relates to a method of manufacturing a sanitary napkin which includes an absorbent body and a layer of resilient material, said method being characterized by the following steps: Fastening together continuous layers of absorbent material and resilient material to form a continuous composite web and then cutting finished sanitary napkins from the continuous web. The invention provides a particularly simple method for the manufacture of sanitary napkins, since, in the case of the present invention, the absorbent body of the napkin need not be enclosed between an inner and an outer casing sheet that extend peripherally beyond the absorbent body and there joined together, as is the case of conventional sanitary napkin manufacture.

In one preferred embodiment of the inventive method, at least one continuous casing sheet is fastened to the continuous sheets of absorbent and resilient material, prior to cutting-out finished napkins.

BRIEF DESCRIPTION OF THE DRAWINGS

The invention will now be described in more detail with reference to the accompanying drawings, in which

FIG. 3 is a schematic perspective view of a second embodiment of an inventive sanitary napkin;

FIG. 4 illustrates schematically a method for manufacturing a sanitary napkin according to a third embodiment of the invention; and FIG. 5 illustrates a sanitary napkin produced by the method illustrated in FIG. 4.

DETAILED DESCRIPTION OF THE PREFERRED EMBODIMENTS

Figure 1:
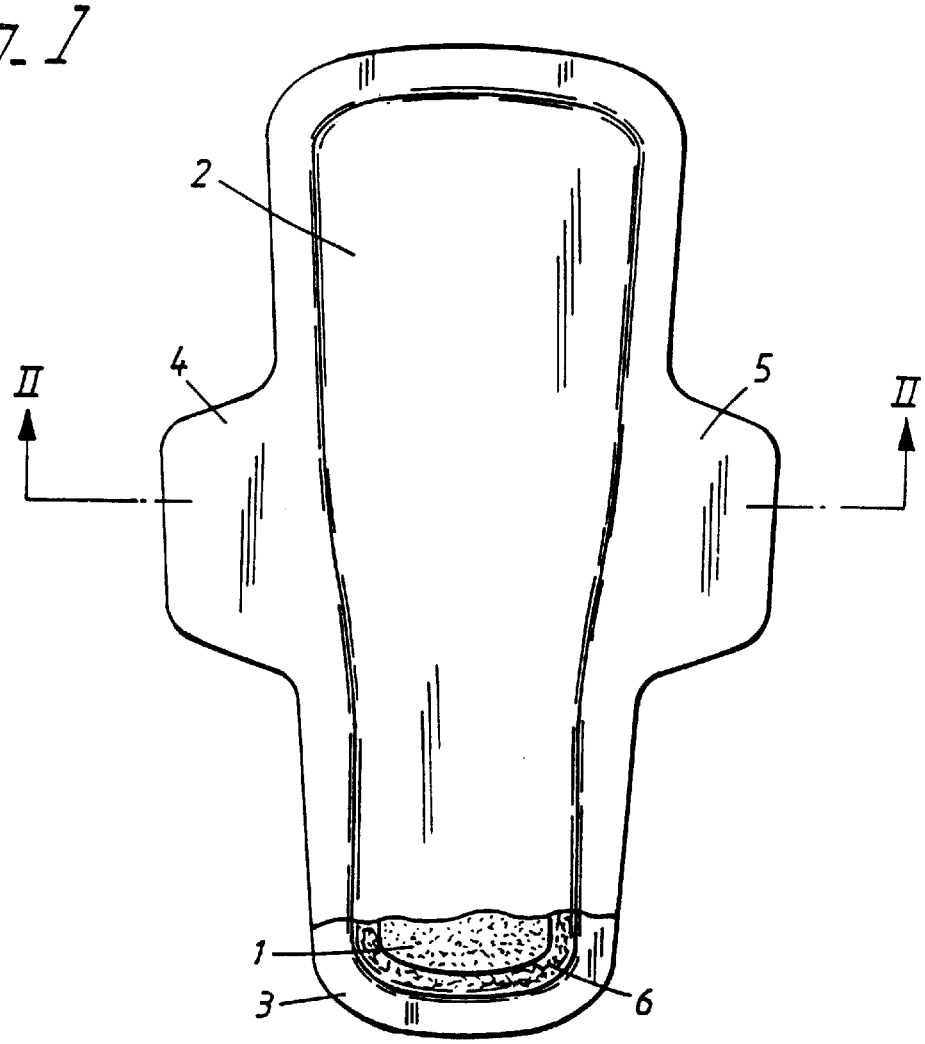
FIG. 1 is a schematic view from above of a first embodiment of an inventive sanitary napkin, with the inner casing sheet partially removed.
Figure 2:
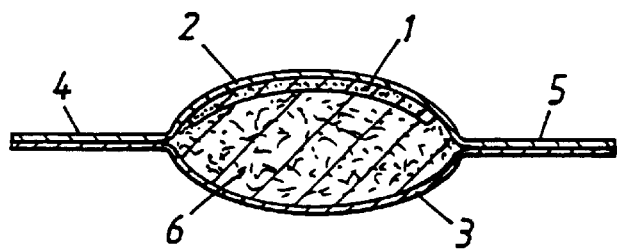
FIG. 2 is a cross-sectional view take on the line II—II in FIG. 1.

The sanitary napkin illustrated in FIGS. 1 and 2 includes an absorbent body 1 enclosed between an inner casing sheet 2 of liquid-permeable material, this layer lying proximal to the wearer's body in use, and an outer casing sheet 3, these sheets extending peripherally beyond the absorbent body and being joined together in regions outside the absorbent body, for instance by gluing or welding. The casing sheets 2, 3 form outwardly protruding flaps 4, 5 in the longitudinal central region of the napkin. When the napkin is fitted into a pair of panties, the flaps 4, 5 are folded around the edges of the panties and fastened to the outside thereof with the aid of suitable, conventional fastener means (not shown), for instance adhesive coatings. The sanitary napkin is also conveniently provided with additional fastener means on the outside of the outer casing sheet, so as to secure the napkin to the inner surface of the panties.

In accordance with the invention, a layer 6 of compressible and resilient material is provided between the absorbent body 1 and the outer casing sheet 3. This layer may suitably be comprised of wadding of the kind used as a spacing layer between the inner casing sheet and the absorbent body of diapers, for instance polyester fibre wadding. Such material will not collapse when wet, which is important for ensuring that the inventive napkin will function as intended even after absorbing a considerable volume of menstrual fluid. Other suitable materials are foamed plastics.

When donning panties in which a sanitary napkin according to the above has been placed, the layer 6 will be compressed as a result of the panty material pressing against the napkin. Since the layer 6 is also resilient, the layer will strive to return to its original thickness, thereby filling out all available space between body and panties within the region of the napkin. A sanitary napkin constructed in accordance with the invention can thus effectively adapt its shape to conform to the available space between the wearer's body and the panties, meaning that no gaps or the like are liable to form between the sanitary napkin and the wearer's body. Menstrual fluid will therefore always be discharged close to the absorbent body, with only a small risk of leakage in the case of the inventive sanitary napkin.

The absorbent body 1 is preferably thin and flexible so as to enable the absorbent body to curve and conform to the wearer's body. This is not totally necessary, however, when the layer of resilient material extends peripherally beyond the absorbent body, so as to lie against the wearer's body when worn, either directly or through the intermediary of inner casing part. In the case of this embodiment, the resilient layer will act as a "seal" and prevent fluid leaking peripherally from the napkin. However, there is preferred an embodiment in which the absorbent body is so flexible as to adapt to the shape of the wearer's body under the influence of the spring force exerted by the resilient layer. The absorbent body can be produced from material which is used typically for this purpose, for instance cellulose fluff, and which has been compressed to a stiffness such as to be able to resist the spring force that is exerted by a layer of resilient material that has been compressed to a maximum, without being further deformed to any appreciable extent.

FIG. 3 illustrates a second embodiment of an inventive sanitary napkin. The napkin of this embodiment includes an absorbent body 7, a layer 8 of non-absorbent, compressible and resilient material, and an outer casing sheet 9. The absorbent body 7 is constructed so as to retain a stable structure and so as not to collapse in a wet state. The body shall also have a good liquid retention capacity. For instance, the absorbent body 7 may be manufactured from a dry-formed sheet material of air-laid cellulose fluff of the kind described in Swedish Patent Application No. 9203445-3. As will be seen from FIG. 3, the resilient layer 8 extends peripherally beyond the rectangular absorbent body 7 and, when the napkin is worn, provides the same sealing effect as that described for the sanitary napkin shown in FIGS. 1 and 2. The layer 8 of the sanitary napkin embodiment shown in FIG. 3 shall also have a barrier effect, so that discharged liquid is unable to penetrate the layer. It has been found that highly viscous menstrual fluid has difficulty in penetrating the wadding that is often used in diapers as a spacing layer nearest the wearer's body, and consequently material of this nature also functions splendidly in a sanitary napkin of the kind illustrated in FIG. 3. This barrier effect also reduces the liquid-impervious requirement placed on the outer casing sheet 9, therewith enabling the outer casing sheet to be comprised of an air-permeable material, such as perforated plastic film or hydrophobic nonwoven material. The outer casing sheet 9 may even be omitted completely.

As will be seen from FIG. 3, the resilient layer 8 is thicker in the longitudinal central region of the napkin than in the remainder of the napkin, so as to ensure that when donning a pair of panties in which such a napkin has been inserted, the layer will be compressed within the region of the wetting point, i.e. the region in which menstrual fluid is normally discharged onto the napkin, so that the absorbent body will be positively pressed against the wearer's body, at least in this region of the napkin. The layer 6 of the embodiment illustrated in FIGS. 1 and 2 may also be formed to advantage in the same way.

A resilient layer of varying thickness can be produced by constructing the layer of two or more resilient bodies of mutually different size and placing these bodies one on top of the other.

The aforesaid barrier effect afforded by those parts of the resilient layer that lie in the plane outside the absorbent body enable a third embodiment of an inventive sanitary napkin to be manufactured in a particular simple fashion. This method is illustrated schematically in FIG. 4, and comprises two manufacturing steps, namely a first step of taking webs of casing material 13, a sheet 14 of absorbent material, and a sheet 15 of nonwoven absorbent-, compressible and resilient material from a respective storage reel 10–12, and combining these webs or sheets and joining them together, for instance by applying an adhesive thereto with the aid of a glue applicator (net shown) and passing the webs through a pair of rolls 16, wherein the second step comprises cutting finished sanitary napkins from the composite web with the aid of a suitable cutting means 17.

FIG. 5 illustrates a sanitary napkin manufactured in accordance with the method shown in FIG. 4. A napkin manufactured in accordance with this method differs from the napkin shown in FIG. 3 by virtue of having an inner casing sheet 13 and lacking an outer casing sheet, and also by virtue of the fact that the resilient layer 15 extends only outside the absorbent body 14 along the longitudinal sides thereof. This can be accepted, however, because side leakage constitutes a much greater problem than end leakage, which is not likely to occur before the total absorption capacity of the absorbent body has been utilized and the napkin has thus been used for a longer period than that for which it is intended.

Inventive sanitary napkins can be packaged with the resilient layer compressed to a maximum and do not therefore take up more room than traditional napkins.

It will be understood that the described exemplifying embodiments can be modified in many ways within the scope of the invention. For example, the napkin shown in FIG. 3 may also be provided with an inner casing sheet, and the napkin shown in FIG. 5 may also be provided with an outer casing sheet, in which case the method illustrated in FIG. 4 is modified by adding a further storage reel containing a continuous web of outer casing material. The sanitary napkin and/or the absorbent bodies may have forms different to those shown in the Figures. Neither need the resilient layer extend laterally beyond the absorbent body, but need only extend to within the region of the wetting point, for instance, i.e. the region within which menstrual fluid is normally discharged when the napkin is worn in the correct position. The invention is therefore only limited by the content of the accompanying claims.

What is claimed is:

1. A sanitary napkin comprising:

an absorbent body; and a layer of compressible and resilient, essentially non-absorbent material located adjacent a surface of the absorbent body which lies distal to a body of a wearer in use, said layer of compressible and resilient material having a surface area extending entirely over said surface of the absorbent body, wherein said layer of compressible and resilient material is thicker in a longitudinal central region of said napkin than in a remainder of the napkin; and wherein said layer of compressible and resilient material is resiliently compressible in a direction perpendicular to said surface of the absorbent body, so as to urge said sanitary napkin to fill out all available space between said sanitary napkin and the body of the wearer during use.

2. The sanitary napkin according to claim 1, wherein the resilient layer also extends around a periphery of the absorbent body.

3. The sanitary napkin according to claim 1, wherein the resilient layer extends beyond longitudinal edges of the absorbent body in a plane parallel with a plane of the absorbent body.

4. The sanitary napkin according to claim 1, wherein the resilient layer is comprised of hydrophobic fibre wadding.

5. The sanitary napkin according to claim 1, wherein the resilient layer is comprised of foamed plastic.

6. The sanitary napkin according to claim 1, wherein the thicker longitudinal central region of the resilient layer is within a wetting region of the napkin.

7. The sanitary napkin according to claim 1, wherein the resilient layer is placed between the absorbent body and an outer casing sheet.

8. The sanitary napkin according to claim 7, wherein the outer casing sheet is comprised of air-permeable material.

9. The sanitary napkin according to claim 1, further comprising an inner casing sheet of liquid-permeable material located adjacent a side of the absorbent body distal from the resilient layer.

10. The sanitary napkin according to claim 1, wherein said resilient layer is adapted to urge said absorbent body toward the wearer.

\* \* \* \* \*